United States Patent
Ballin

(10) Patent No.: US 7,195,606 B2
(45) Date of Patent: Mar. 27, 2007

(54) SYRINGE AND A METHOD FOR ITS UTILIZATION IN ANALYSIS

(75) Inventor: Ben-Ami Ballin, Givat Shmuel (IL)

(73) Assignee: ErythroSave Ltd., Migdal Ha Emek (IL)

( * ) Notice: Subject to any disclaimer, the term of this patent is extended or adjusted under 35 U.S.C. 154(b) by 364 days.

(21) Appl. No.: 10/467,057

(22) PCT Filed: Feb. 19, 2002

(86) PCT No.: PCT/IL02/00126

§ 371 (c)(1),
(2), (4) Date: Aug. 18, 2003

(87) PCT Pub. No.: WO02/067778

PCT Pub. Date: Sep. 6, 2002

(65) Prior Publication Data

US 2005/0261620 A1   Nov. 24, 2005

(30) Foreign Application Priority Data

Feb. 26, 2001 (IL) .................................. 141651
Dec. 27, 2001 (IL) .................................. 147373

(51) Int. Cl.
A61M 37/00 (2006.01)
A61M 5/00 (2006.01)
C02F 1/38 (2006.01)
B65D 81/00 (2006.01)

(52) U.S. Cl. .................. 604/6.01; 604/6.02; 604/6.04; 604/187; 604/231; 210/782; 600/577

(58) Field of Classification Search ............... 604/4.01, 604/5.01, 6.01, 6.04, 6.05, 6.15, 19, 27, 264, 604/218, 220, 223, 226, 231, 232, 236, 238, 604/86–91; 210/781, 789; 435/2, 372; 600/576–578, 600/573, 581; 422/44; 424/529–530; 494/16
See application file for complete search history.

(56) References Cited

U.S. PATENT DOCUMENTS

| 701,671 A | * | 6/1902 | Billings ...................... 604/125 |
| 3,596,652 A | * | 8/1971 | Winkelman .................. 600/575 |
| 3,706,305 A | * | 12/1972 | Berger et al. ................ 600/575 |

(Continued)

FOREIGN PATENT DOCUMENTS

| EP | 1092447 | 4/2001 |
| WO | WO 8802258 | 4/1988 |
| WO | WO 01/23017 | 4/2001 |

OTHER PUBLICATIONS

Ballin, et al. Evaluation of a New Method for the Prevention of Neonatal Anemia:, Pediatric Research; vol. 25, No. 3 pp. 174-175.
Apr. 18, 2005, European Search Report EP 02712228.
Oct. 15, 1987, esp@cenet copy of DE3607227, no translation attached.

*Primary Examiner*—Tatyana Zalukaeva
*Assistant Examiner*—Leslie Deak
(74) *Attorney, Agent, or Firm*—Neifeld IP Law, PC

(57) ABSTRACT

The invention provides a syringe for preventing anemia resulting from withdrawal of blood from a patient for analysis, the syringe including a cylindrical tube having a nozzle at its lower end to which a needle is attachable; a piston disposed within the tube and apiston handle protruding from the upper end of hte tube; the syringe being further adapted to a be placed in a centrifuge for separating blood drawn from the patient into supernatant plasma component and a packed-cells component, and further comprising means for separating or removing at least a portion of teh plasma, thereby facilitating the injection of the packed-cells back into the patient The invention also provides a method for preventing anemia resulting from the withdrawal of blood from a patient for analysis.

7 Claims, 5 Drawing Sheets

U.S. PATENT DOCUMENTS

| | | | |
|---|---|---|---|
| 3,750,645 A * | 8/1973 | Bennett et al. | 600/573 |
| 3,826,622 A * | 7/1974 | Natelson | 422/102 |
| 3,849,072 A * | 11/1974 | Ayres | 210/789 |
| 3,943,917 A | 3/1976 | Johansen | |
| 4,685,910 A * | 8/1987 | Schweizer | 604/218 |
| 4,957,637 A * | 9/1990 | Cornell | 210/782 |
| 5,032,117 A | 7/1991 | Motta | |
| 5,429,603 A | 7/1995 | Morris | |
| 5,577,513 A * | 11/1996 | Van Vlasselaer | 600/578 |
| 5,592,948 A | 1/1997 | Gatten | |
| 5,674,195 A * | 10/1997 | Truthan | 604/87 |
| 5,779,668 A * | 7/1998 | Grabenkort | 604/89 |
| 6,013,037 A * | 1/2000 | Brannon | 600/576 |
| 6,706,008 B2 * | 3/2004 | Vishnoi et al. | 604/5.01 |

* cited by examiner

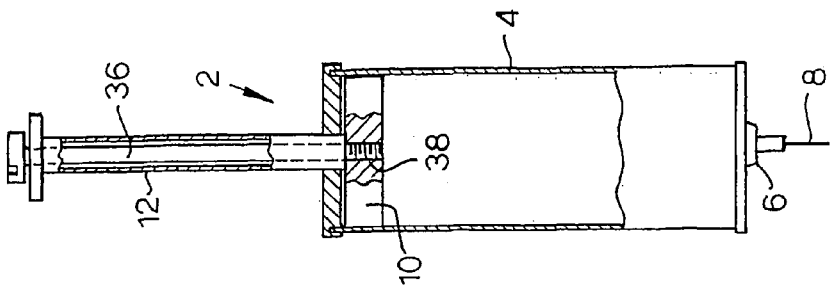
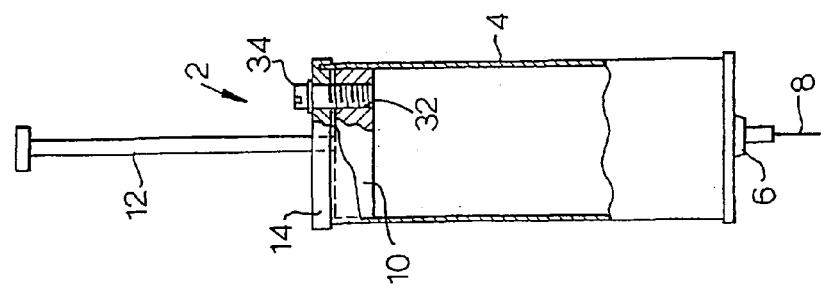
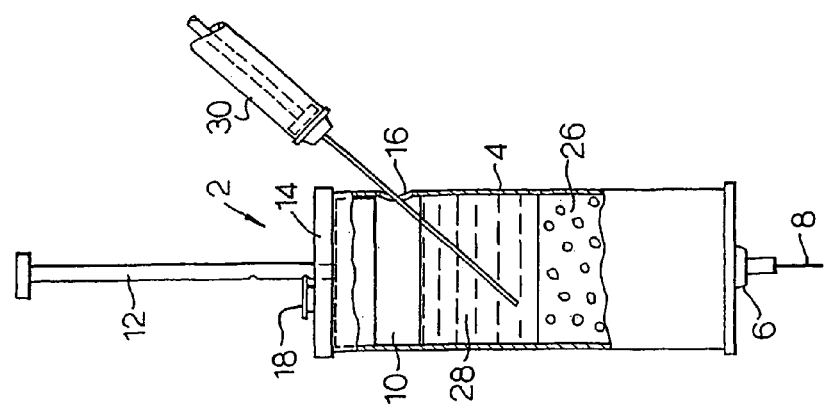
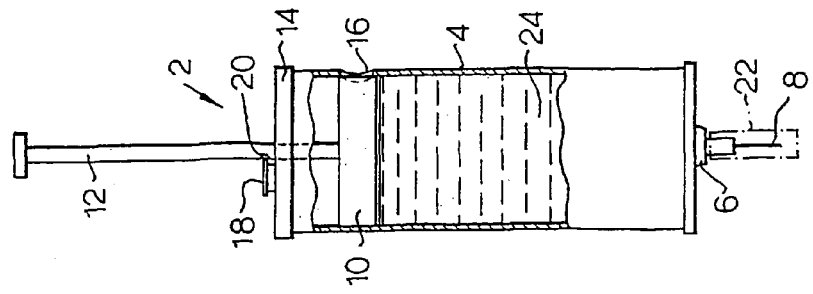

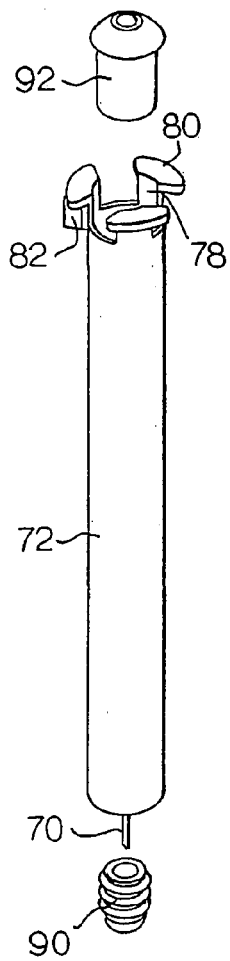
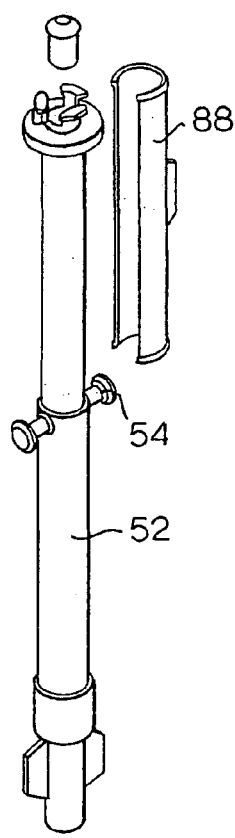
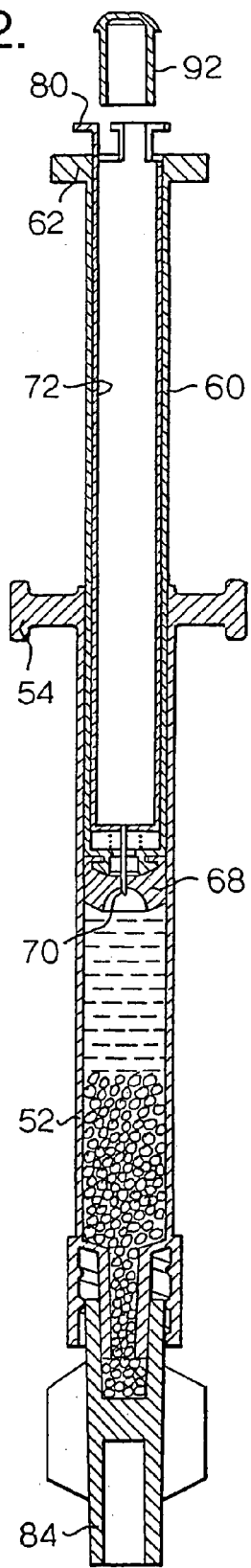

SYRINGE AND A METHOD FOR ITS UTILIZATION IN ANALYSIS

FIELD OF THE INVENTION

The present invention relates to a method for preventing anemia in patients, specifically, in premature infants, and to a syringe to be used in the method. More particularly, the invention concerns a combined syringe and blood sampling and centrifuge device and to a method for drawing blood from infants for analysis while preserving the erythrocytes.

BACKGROUND OF THE INVENTION

One of the main reasons for anemia in premature infants is blood withdrawal from them for diagnostic purposes. During their first days of life, infants weighing less than 1500 grams, whose blood volume is less than 120 ml, are often subjected to blood withdrawal, as a result of which they inevitably have to be transfused with packed-cells. Some infants receive the equivalent of a double- or triple-volume red cell exchange transfusion as a result of blood sampling for laboratory tests. The premature infants are exposed to all of the side effects of blood transfusions, including infections due to agents transmitted by blood (CMV, HIV, hepatitis), volume overload, mechanical erythrocyte injury, alloimmunization, and more.

DISCLOSURE OF THE INVENTION

It is therefore a broad object of the present, invention to overcome the above-mentioned problems and to provide a method for blood withdrawal from infants that will prevent anemia, and a combined syringe and blood sampling and centrifuge device for use in that method.

The principle behind the invention is to draw the blood through an arterial or venous line, to spin it as a bedside procedure, to remove the plasma for laboratory analysis and to administer the erythrocytes back to the patient through the same arterial or venous line. The procedure is carried out by the same syringe, without transferring the whole sample or its components (plasma and packed-cells) to any additional tube or syringe.

Thus, the invention provides a syringe for preventing anemia resulting from withdrawal of blood from a patient for analysis, the syringe comprising tube having a nozzle at its lower end to which a needle is attachable, a piston disposed within the tube and a piston handle protruding from the upper end of the tube; the syringe being further adapted to be placed in a centrifuge for separating blood drawn from the patient into a supernatant plasma component and a packed-cells component, and further comprising means for separating or removing at least a portion of the plasma, thereby facilitating the injection of the packed-cells back into the patient.

The invention also provides a syringe for preventing anemia resulting from withdrawal of blood from a patient for analysis, the syringe comprising a syringe body having, at its lower end, a nozzle to which means for connection to a patient's blood vessel are attachable; a hollow, cylindrical piston rod slidably disposed in the syringe body and carrying, at its lower end, a piston sealingly fitting the syringe body, the piston rod having a gripping disk at its upper end; a plasma vessel disposed within and slidingly fitting the hollow piston rod, the lower end of the vessel being closed and carrying a hollow needle through which a liquid can enter the vessel; wherein, by pulling up the piston rod, whole blood from the patient is drawn into the syringe body, the whole blood then being separated by centrifuging into a plasma component and a packed-cells component, and wherein, subsequently, by applying force to the upper, protruding end of the plasma vessel, the hollow needle is caused to perforate the piston, whereupon pushing down the piston rod causes the separated plasma component to be forced through the needle into the plasma vessel.

The invention further provides a method for preventing anemia resulting from the withdrawal of blood from a patient for analysis, the method comprising providing a syringe as described herein and affixing a needle to its nozzle; drawing blood from the patient; removing the needle or covering it and/or the nozzle with a valve; introducing the syringe into a centrifuge and centrifuging the blood sample, causing the blood to be divided into a supernatant plasma component and a packed-cells component; removing at least a portion of the supernatant plasma component from the syringe; removing the valve from the nozzle and needle; affixing a new needle to the syringe, and injecting at least a portion of said packed-cells component back into the patient.

The invention still further provides a method for preventing anemia resulting from the withdrawal of blood from a patient for analysis, the method comprising providing a syringe as described herein and affixing means for connection to a blood vessel of the patient; drawing blood from the patient; removing the means for connection to a blood vessel of the patient; closing the nozzle by means of the stopper; introducing the syringe into a centrifuge and centrifuging the blood sample, thus causing the blood to be divided into a supernatant plasma component and a packed-cells component; removing the syringe from the centrifuge and removing the lock means from the piston rod; removing the safety tab from the upper end portion of the plasma vessel and pushing down the vessel to perforate the piston; pushing the piston rod until the piston reaches the interface between the supernatant plasma component and the packed-cells component, and withdrawing the plasma vessel and performing analysis of the plasma.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1 and 2 are schematic, cross-sectional views of a first embodiment of a syringe according to the present invention, illustrating its two states of operation;

FIGS. 3 and 4 are schematic, cross-sectional views of further embodiments of a syringe according to the invention;

Figure 5A:
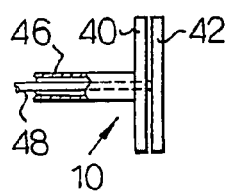
Figure 5B:
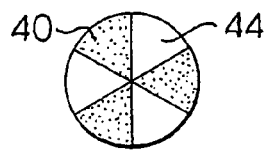
Figure 5C:
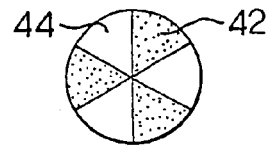
Figure 7:
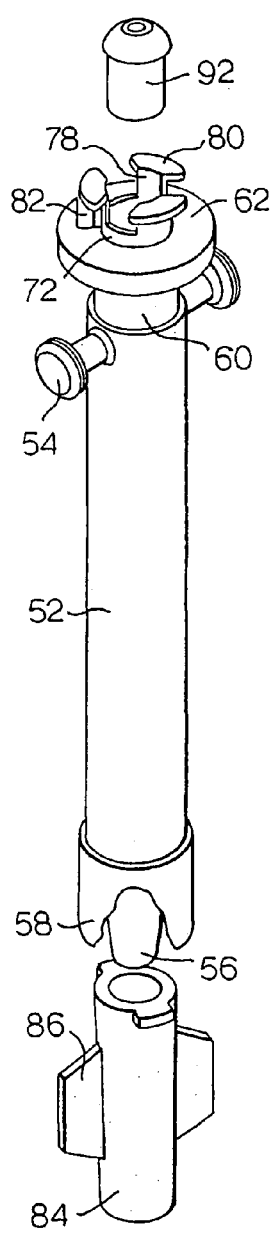
Figure 8:
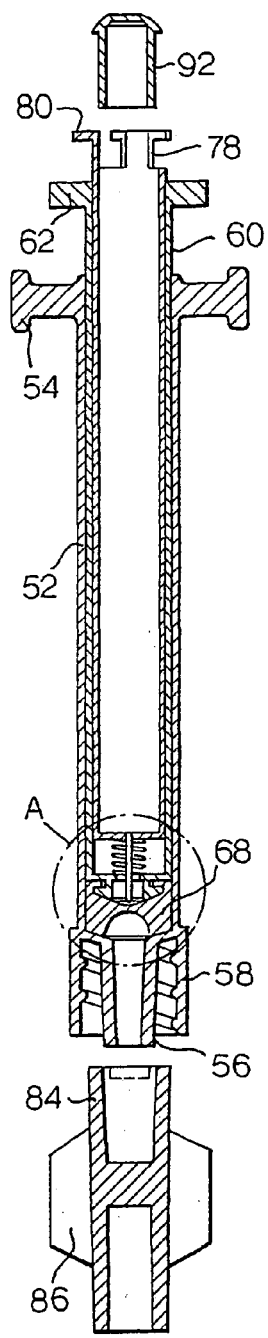
Figure 9:
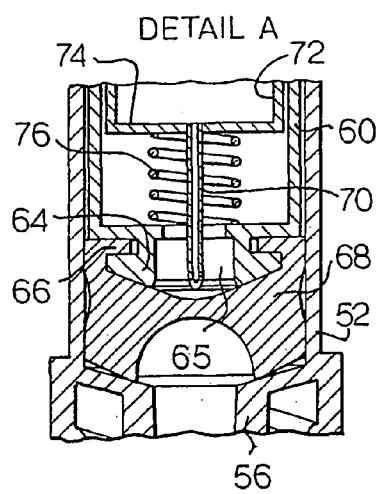

FIGS. 5A–5C schematically illustrate an embodiment of a piston arrangement for the embodiment of FIGS. 6A–6F;

FIGS. 6A–6F are schematic cross-sectional views of a syringe according to the invention, utilizing the piston arrangement of FIGS. 5A–5C, showing different states of operation;

FIG. 7 is a semi-exploded perspective view of yet another embodiment of the syringe according to the present invention;

FIG. 8 is a cross-sectional view of the embodiment of FIG. 1;

FIG. 9 is an enlarged view of detail A in FIG. 8;

FIG. 10 is a perspective view of the plasma vessel and its attachments;

FIG. 11 represents the syringe prior to centrifuging and prior to the mounting of a safety lock, and FIG. 12 is a cross-sectional view showing the syringe after centrifuging and perforation of the piston.

DETAILED DESCRIPTION

FIGS. 1 and 2 illustrate a first embodiment of a syringe 2 for preventing anemia due to frequent withdrawal of blood for analysis, especially in premature infants. The syringe 2 comprises a cylindrical tube 4 having a nozzle 6 at its lower end to which a needle 8 is attachable, a piston 10 to which is affixed an operating handle 12 protruding from the upper end of tube 4 through a cover 14. Contrary to common syringes, syringe 2 is further provided with an aperture 16 in the upper wall portion of tube 4, at a location below its upper edge, so that the thickness of piston 10 will not obstruct the aperture 16 when the piston is drawn to the upper end of the tube, as illustrated in FIG. 2. In order to assure that the piston will obstruct and close aperture 16 during the part of the procedure when same is required, there is advantageously provided a locking means 18, such as a swiveling arm pivotably coupled to cover 14 at one end and having a pin engageable with a hole 20 in handle 12, at its other end.

In accordance with the method of the invention, the syringe operates as follows: blood is drawn from the patient into syringe 2. The piston 10 is then secured in a position so as to align the periphery of the piston with, and close, the aperture 16, a valve 22 is fitted over the nozzle 6, whether or not the needle 8 has first been removed, and the syringe containing the blood sample 24 is placed in a commonly used and available centrifuge (not shown). Centrifuging of the sample will cause it to divide into two components: a lower component, essentially constituting packed-cells 26, above which the upper component, plasma 28, accumulates. The means 18 are then moved to release handle 12, which is then pulled above aperture 16. The plasma 28, or a portion thereof, is sucked out of syringe 2 through aperture 16 into another syringe or suction device 30, for analysis (FIG. 2). Valve 22 is then removed, syringe 4 is fitted with a fresh needle 8 and cells 26 are reintroduced into the patient's bloodstream, replenishing the cells and avoiding erythrocyte deficiency.

Modifications of the structure of the syringe 2 are illustrated in FIGS. 3 and 4. In FIG. 3, the syringe includes a piston 10 having an aperture 32 which is normally closed by any suitable removable plug, such as a screw 34 passing through the cover 14. After centrifuging, the plug is removed and the plasma is withdrawn from the syringe 2 by means of a suction device penetrating through the piston aperture 32, the screw 34 is replaced and the remaining plasma with cells can be injected back into the patient.

FIG. 4 illustrates a hollow handle 12, through which an elongated screw 36 is attached to the piston 10. After centrifuging, the screw 36 and possibly the entire handle 12 is removed, thus forming an aperture 38 in the piston. The plasma is removed through aperture 38 by means of a suction device having a needle, and similar to the embodiment of FIG. 3, the remaining plasma containing. cells is injected back into the patient.

A still further embodiment of the syringe according to the present invention is shown in FIGS. 5A, 5B and 5C. Piston 10 of the syringe consists of two disks 40, 42, each made in the illustrated case with identically shaped triangular apertures 44. Disk 40 is attached to an outer tubular handle 46, while disk 42 is attached to a rod 48 concentrically disposed inside tubular handle 46. Rod 48, together with disk 42, is rotatable with respect to handle 46 and disk 40, thereby facilitating, in a first state, the alignment of apertures 44 in the two disks 40, 42. In its second state, the alignment of the apertures is removed, so that the apertures in disk 40 are obscured by disk 42, forming a contiguous, non-apertured piston surface.

The step-by-step method of operation of an embodiment of a syringe utilizing the piston of FIGS. 5A–5C is illustrated in FIGS. 6A to 6F.

Figure 6A:
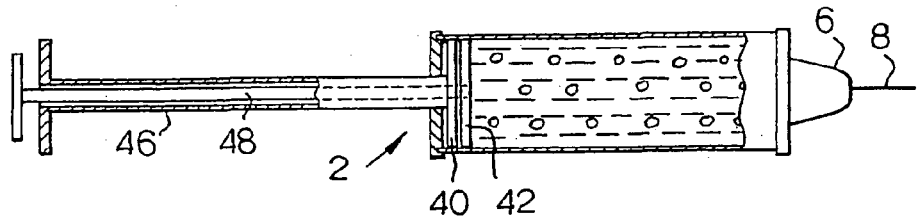
Figure 6B:
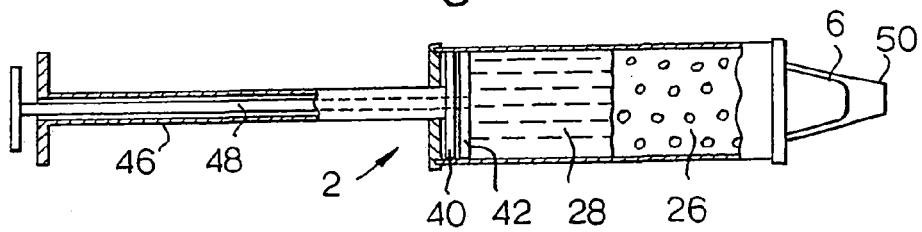
Figure 6C:
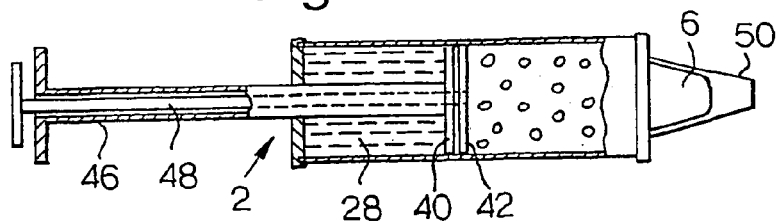
Figure 6D:
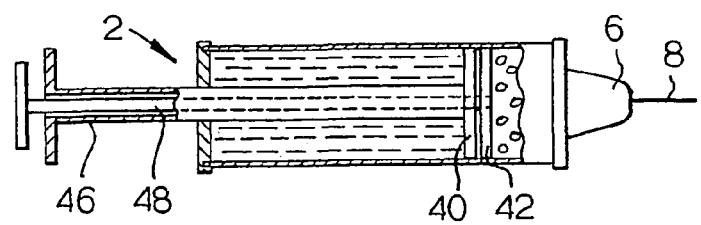
Figure 6E:
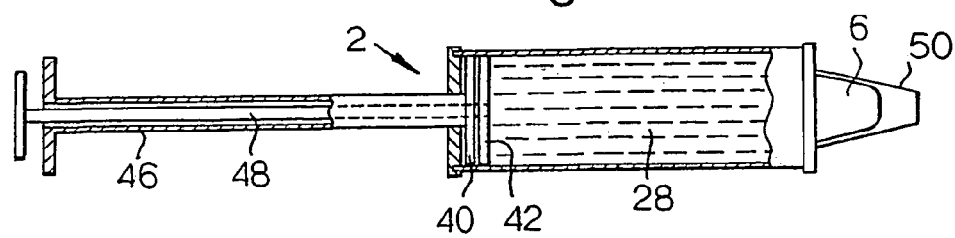
Figure 6F:
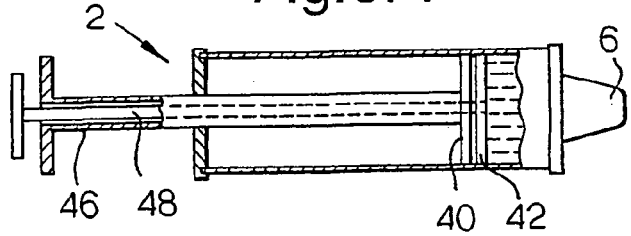

FIG. 6A illustrates the syringe after blood is withdrawn from a patient. The withdrawal of the blood required the forming of a non-apertured piston surface, as explained above with respect to FIGS. 5A–5C. Shown is, the blood, comprising intermixed blood cells and plasma. The nozzle 6 is then covered with a cap or valve 50 (FIG. 6B) and the entire syringe is placed in a centrifuge. Centrifuging causes a clear division between the blood cells 26 and plasma 28. Disk 42 is then turned by means of rod 48, so as to form an apertured piston. Piston 10 is pushed inside tube 4 to a position between the two blood components, namely, between cells 26 and plasma 28 (FIG. 6C). Rod 48 is then turned again so as to close apertures 44, forming a single piston surface. The valve 50 is removed, a fresh, sterile needle 8 is fitted into nozzle 6, and the cells 26 are reinjected into the patient (FIG. 6D). The piston is brought into its open state, enabling it to be pulled back through the plasma in the syringe (FIG. 6E). The piston is then brought into its closed state, thus enabling the plasma 28 in the syringe to be directly ejected into a test tube by means of the piston (FIG. 6F).

FIGS. 7–12 illustrate yet another embodiment of the syringe according to the invention. There is seen in FIG. 7 a syringe body 52, provided with a pair of trunnions 54 on which the syringe can be hung into the centrifuge. The lower end of syringe body 52 is in the form of a tapered nozzle or tip 56, advantageously of the male luer-lock type with its internally threaded sleeve 58, to which tip a hypodermic needle, a catheter with an integral female luer-lock terminal, and other accessories are connectable.

Inside syringe body 52 there is slidably disposed a hollow piston rod 60, seen to better effect in FIGS. 8 and 9. Piston rod 60 has a gripping disk 62 at its upper end, and an undercut head 64 with a central bore 65 at its lower end. The inward-pointing rim 66 of a piston 68, made of an elastomer, engages in the undercut. As seen in FIG. 9, the cross-section of piston 68 is greatly reduced in the central portion, with a hollow needle 70 poised above, but not touching, that weakened point. The purpose of this arrangement will be explained further below.

Inside hollow piston rod 60, there is slidingly accommodated a vessel 72, designed to accept the blood plasma after its separation, by centrifuging, from the erythrocytes. As can be seen in FIG. 9, the hollow needle 70 is fixedly attached to bottom 74 of vessel 72. A helical compression spring 76 is interposed between bottom 74 of vessel 72 and head 64 of piston rod 60. When in the position shown in FIGS. 7 and 8, the upper end of vessel 72 projects from gripping disk 62 and is seen to consist of three prongs 78 topped by pads 80. Also seen is a safety tab 82, designed to prevent needle 70 from inadvertently perforating piston 68. When perforation is required, safety tab 82 is simply broken off.

Further shown in FIGS. 7 and 8 is a stopper 84, in the form of a female luer-lock connector having two wings 86 for handling. Stopper 84 is applied after the required quantity of whole blood has been drawn, prior to centrifuging of the sample.

The procedure for using the syringe according to the invention is as follows:

A hypodermic needle or a catheter is used to attach the syringe to one of the patient's blood vessels and the required quantity of whole blood is drawn. After that, the needle or catheter is detached from the syringe and stopper 84 is mounted on nozzle 56. A lock 88 is clipped onto piston rod 60, to prevent centrifugal force acting on the syringe from exerting pressure on the syringe. Then, the syringe, now with the greatly extended piston rod 60 in the position shown in FIG. 11, is introduced into the centrifuge. After centrifuging has been concluded and the whole-blood content of the syringe has been separated into the packed-cells component and the supernatant plasma component, the syringe is removed from the centrifuge, safety tab 82 is broken off, disk 62 is held between the index and middle fingers, and pressure is applied by the thumb on pads 80, causing needle 70 to perforate piston 68 (FIG. 12). The perforation establishes a pathway between syringe body 52, now full with the separated, packed blood cells, and the supernatant plasma.

Now, piston rod 60 is pushed down. Since nozzle 56 is closed by stopper 84, the descending piston 68 causes the plasma to pass through needle 70 into plasma vessel 72. Piston 68 is pushed down until it reaches the interface between the plasma and the packed-cells. At that point, pressure on pads 80 is relaxed and spring 76 withdraws needle 70 from piston 68 by lifting vessel 72, thereby hermetically closing off the packed cell component remaining in the syringe due to the resilient elastomer of piston 68.

Plasma vessel 72 is now withdrawn from piston rod 62, needle 70 is secured by means of a rubber plug 90, the upper end of vessel 72 is closed with a plug 92, and vessel 72, along with its plasma contents, is transferred to the laboratory for analysis.

As a last step, stopper 84 is replaced by a hypodermic needle or a catheter, and the packed-cells component is returned to the patient's blood vessel.

Other types of pistons in which an aperture can controllably be formed are also envisioned.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A syringe for withdrawal of blood from a patient and for subsequent injection of at least part of the blood components back into the patient, said syringe comprising:

a syringe body having, at its lower end, a nozzle to which means for connection to a patient's blood vessel are attachable;

a hollow, cylindrical piston rod having an inner bottom surface and being slidably disposed in said syringe body and carrying, at its lower end, a piston sealingly fitting said body, said piston rod having a gripping disk at its upper end;

a plasma vessel disposed within and slidingly fitting said hollow piston rod, the lower end of said vessel being closed and carrying a hollow needle through which a liquid can enter said vessel via said hollow needle;

a helical compression spring surrounding said needle and positioned between said plasma vessel and said inner bottom surface of said piston rod;

wherein, by pulling up said piston rod, whole blood from said patient is drawn into said syringe body, said whole blood then being separated by centrifuging into a plasma component and a packed-cells component; and wherein, subsequently, by applying force to the upper, protruding end of said plasma vessel, said hollow needle is caused to perforate said piston, whereupon pushing down said piston rod causes said separate plasma component to be forced through said needle into said plasma vessel;

whereinafter, when ceasing to apply said force to said end, said hollow needle is withdrawn from said piston by the restoring force of said spring.

2. The syringe as claimed in claim 1, further comprising stopper means to seal off said nozzle prior to said centrifuging.

3. The syringe as claimed in claim 1, further comprising lock means for maintaining the relative positions of said hollow piston rod and said syringe body during said centrifuging.

4. The syringe as claimed in claim 1, further comprising a removable safety tab at the upper end portion of said plasma vessel, for preventing the inadvertent perforation of the piston.

5. The syringe as claimed in claim 1, further comprising a pair of trunnions fixedly attached to, or integral with, said syringe body, to mount said syringe on a centrifuge.

6. A method for withdrawal of blood from a patient and for subsequent injection of at least part of the blood components back into the patient, said method comprising:

providing a syringe body having, at its lower end, a nozzle to which means for connection to a patient's blood vessel are attachable; a hollow, cylindrical piston rod having an inner bottom surface and being slidably disposed in said syringe body and carrying, at its lower end, a piston sealingly fitting said body, said piston rod having a gripping disk at its upper end; a plasma vessel disposed within and slidingly fitting said hollow piston rod, the lower end of said vessel being closed and carrying a hollow needle through which a liquid can enter said vessel via said hollow needle; a helical compression spring surrounding said needle and positioned between said plasma vessel and said inner bottom surface of said piston rod, and affixing means for connection to a blood vessel of said patient;

drawing blood from said patient;

removing said means for connection to a blood vessel of said patient;

closing said nozzle by means of said stopper;

introducing said syringe into a centrifuge and centrifuging the blood sample, thus causing the blood to be divided into a supernatant plasma component and a packed cells component;

removing said syringe from the centrifuge and removing a lock means from said piston rod;

removing said safety tab from the upper end portion of said plasma vessel and pushing down the vessel to perforate said piston;

pushing said piston rod until the piston reaches the interface between said supernatant plasma component and said packed cells component, and withdrawing said plasma vessel and performing analysis of said plasma.

7. The method as claimed in claim 6, comprising the further steps of:

removing a stopper from said nozzle;

affixing means for connection to a blood vessel of said patient to said nozzle, and injecting at least part of said packed cells component back into the patient's blood vessel.

* * * * *